United States Patent [19]

Harris et al.

[11] Patent Number: 5,102,900
[45] Date of Patent: Apr. 7, 1992

[54] IMIDAZOLES USEFUL AS ANTIATHEROSCLEROTIC AGENTS

[75] Inventors: Neil V. Harris, Tilbury; Christopher Smith, Thundersley, both of England

[73] Assignee: Rhone-Poulenc Rorer S.A., Antony Cedex, France

[21] Appl. No.: 588,871

[22] Filed: Sep. 27, 1990

[30] Foreign Application Priority Data

Sep. 27, 1989 [GB] United Kingdom ................ 8921793
Jul. 27, 1990 [GB] United Kingdom ................ 9016494

[51] Int. Cl.$^5$ .................. A61K 31/415; C07D 405/04
[52] U.S. Cl. ..................................... 514/397; 548/336
[58] Field of Search ........................ 548/336; 514/397

[56] References Cited

U.S. PATENT DOCUMENTS 4,315,021  2/1982  Kluge et al. .......................... 514/397
4,992,421  2/1991  De et al. ............................... 548/336
4,992,457  2/1991  Schulman et al. ................... 514/397

Primary Examiner—Mary C. Lee
Assistant Examiner—Lenora Miltenberger
Attorney, Agent, or Firm—Morgan & Finnegan

[57] ABSTRACT

Imidazole derivatives of the formula:

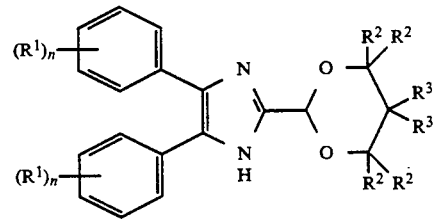

are described wherein $R^1$ represents halogen, alkyl or alkoxy, n is 0 to 5, $R^2$ represents hydrogen or alkyl, $R^3$ represents hydrogen or alkyl optionally substituted by halogen, hydroxy, acyloxy, alkoxy, hydroxyalkoxy, acyloxyalkoxy, or by optionally substituted phenyl, or the groups $R^3$ and the carbon atom to which they are attached together form a cycloalkane or cycloalkene group. They are pharmaceutically useful as antiatherosclerotic agents.

9 Claims, No Drawings

IMIDAZOLES USEFUL AS ANTIATHEROSCLEROTIC AGENTS

FIELD OF THE INVENTION

This invention relates to new, therapeutically useful imidazole derivatives, to a process for their production and to pharmaceutical compositions containing them.

DETAILED DESCRIPTION OF THE INVENTION

The new imidazole derivatives of the present invention are the compounds of general formula I, hereinafter depicted, wherein the symbols R, are the same or different and each represents a halogen atom or an alkyl or alkoxy group containing from 1 to 3 carbon atoms, the symbols n are the same or different and each represents 0 or an integer from 1 to 5, the symbols $R_2$ are the same or different and each represents a hydrogen atom or an alkyl group containing from 1 to 3 carbon atoms, and the symbols $R_3$ are the same or different and each represents a hydrogen atom or an alkyl group containing from 1 to 3 carbon atoms optionally substituted by one or more halogen atoms, by a hydroxy or acyloxy group, by an alkoxy group containing from 1 to 3 carbon atoms which itself is optionally substituted by a hydroxy or acyloxy group, or by a phenyl group which itself is optionally substituted by one or more substituents selected from halogen atoms and alkyl and alkoxy groups each containing up to 3 carbon atoms, or together the symbols $R_3$ and the carbon atom to which they are both attached form a cycloalkane or cycloalkene group containing from 5 to 7 carbon atoms, and pharmaceutically acceptable salts thereof.

In the above definition of $R_3$, the term "acyloxy" preferably means an alkanoyloxy group containing up to 6 carbon atoms or a benzoyloxy group.

By the term "pharmaceutically acceptable salts" as used in this specification is meant acid addition salts, the anions of which are relatively innocuous to the animal organism when used in therapeutic doses so that the beneficial pharmaceutical properties of the parent compounds of formula I are not vitiated by side-effects ascribable to those anions.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

In this specification reference to compounds of formula I is intended to included reference to their pharmaceutically acceptable salts, where the context so permits.

As will be apparent to those skilled in the art, some of the compounds of formula I exhibit optical and/or geometric isomerism. All such forms, and their mixtures, are embraced by the invention.

Preferably the groups $R^1$ are identical.

Preferably the symbols n are identical. Preferably n is 0 or 1; and when n is 1, the corresponding group $R^1$ is preferably in the paraposition of the phenyl group to which it is attached.

Preferably the groups $(R^1)_n$ on each phenyl ring, including their patterns of substitution on the phenyl rings in relation to the points of attachment of the phenyl rings to the rest of the molecule, are identical.

Preferably at least one of each geminal pair of symbols $R^2$ represents a hydrogen atom, and preferably symbols $R^2$ which do not represent hydrogen atoms are identical.

Compounds in which R is halogen or alkyl and $R^2$ and $R^3$ are hydrogen or alkyl ar also preferred.

Especially important compounds of the present invention include those wherein at least one of the symbols has a value selected from the following:
(i) n represent 0 or 1;
(ii) $R^1$ represents a methyl or methoxy group;
(iii) $R^2$ represents a hydrogen atom or a methyl group;
(iv) $R^3$ represents a hydrogen atom or an alkyl group containing 1 or 2 carbon atoms optionally substituted by a hydroxy, acyloxy, e.g. acetoxy, methoxy or phenyl group, or together the symbols $R^3$ and the carbon atom to which they are both attached form a cyclohexane or cyclohexene group; the other symbols being as hereinbefore defined, and pharmaceutically acceptable salts thereof.

Particularly important compounds according to the invention include the following:
A: 2-(1,3-dioxan-2-yl)-4,5-diphenylimidazole;
B: 2-(5,5-dimethyl-1,3-dioxan-2-yl)-4,5-diphenylimidazole;
C: (±)-cis/trans-2-(4,6-dimethyl-1,3-dioxan-2-yl)-4,5-diphenylimidazole;
D: r-2-(4,5-diphenylimidazol-2 -yl) -c-5-hydroxymethyl-5-methyl-1,3-dioxane;
E: r-2-(4,5-diphenylimidazol-2-yl)-t-5-hydroxymethyl-5-methyl-1,3-dioxane;
F: r-2-(4,5-diphenylimidazol-2-yl)-5-ethyl-c-5-hydroxymethyl-1,3-dioxane;
G: r-2-(4,5-diphenylimidazol-2-yl) -t-5-methoxymethyl-5-methyl-1,3-dioxane;
H: r-2-(4,5-diphenylimidazol-2-yl)-c-5-methoxymethyl-5-methyl-1,3-dioxane;
I: r-2-(4,5-diphenylimidazol-2-yl)-5-ethyl-c-5-methoxymethyl-1,3-dioxane;
J: cis-5-benzyl-2-(4,5-diphenylimidazol-2-yl)-1,3-dioxane;
K: trans-5-benzyl-2-(4,5-diphenylimidazol-2-yl)-1,3-dioxane;
L: 2-(4,5-diphenylimidazol-2-yl)-1,3-dioxane-5-spirocyclohexane;
M: 2-(4,5-diphenylimidazol-2-yl)-1,3-dioxane-5-spirocyclohex-3'-ene;
N: 5,5-bis(ethoxymethyl)-2-(4,5-diphenylimidazol-2-yl)-1,3-dioxane;
O: 2-(4,5-diphenylimidazol-2-yl)-5,5-diethyl-1,3-dioxane;
P: 2-[4,5-bis(4-methoxyphenyl)imidazol-2-yl]-5,5-dimethyl-1,3-dioxane;
Q: 2-[4,5-bis(4-methylphenyl)imidazol-2-yl]-5,5-dimethyl-1,3-dioxane;
R: t-5-acetoxymethyl-r-2-(4,5-diphenylimidazol-2-yl)-5-methyl-1,3-dioxane; and
S: 2-(4,5-diphenylimidazol-2-yl)-5,5-bis(hydroxymethyl)-1,3-dioxane.

The letters A to S are allocated for easy reference later in this specification.

The compounds according to the invention are inhibitors of acyl coenzyme-A:cholesterol-O-acyl transferase (ACAT;EC 2.3.1.26). They are therefore of value as anti-atherosclerotic agents and have utility in the treatment or prevention of conditions such as atherosclerosis, hyperlipidemia, cholesterol ester storage disease and atheroma in vein grafts.

In assays performed in vitro microsomes, prepared from the livers of rats fed a diet supplemented with 0.5% w/w cholesterol and 0.25% w/w cholic acid for 7 days, were incubated with radiolabelled oleoyl-CoA in the presence of compounds according to the invention at a concentration of 1μg/ml. The degree of ACAT inhibition produced is shown in Table 1.

In in vivo tests, using rats fed on a similar diet to that above and further supplemented by 0.03% w/w of test compound, compounds according to the invention inhibited increases in plasma cholesterol level, measured after 3 days, relative to control animals fed on the cholesterol supplemented diet without the drug, as shown in Table 1. Values of 100% or more indicate plasma cholesterol concentrations that were similar to those of control rats fed on a normal (non-supplemented) diet.

TABLE 1

| Compound | In-vitro % Inhibition | In-vivo % Reduction |
|---|---|---|
| A | 94 | 86 |
| B | 95 | 105 |
| C | 74 | |

Compounds of formula I can be prepared by the application or adaptation of known methods, by which is meant methods used heretofore or described in the literature.

According to a feature of the present invention, compounds of general formula I are prepared by the replacement by hydrogen of the group $R^4$ of a compound of the general formula II hereinafter depicted, wherein $R^1$, $R^2$, $R^3$ and n are as hereinbefore defined and $R^4$ represents a protecting group, for example a benzyl group, by the application or adaptation of known methods. For example, when $R^4$ is a benzyl group, it is replaced by a hydrogen atom preferably by treatment with sodium in liquid ammonia.

Compounds of formula II may be prepared by the reaction of compounds of the general formula III hereinafter depicted with compounds of the general formula:

$$HOC(R^2)_2C(R^3)_2C(R^2)_2OH \qquad IV$$

wherein $R^2$ and $R^3$ are as hereinbefore defined. The reaction is generally carried out in an inert organic solvent in the presence of an acidic catalyst. Conveniently, the reaction is carried out in toluene as the solvent, with pyridinium 4-toluenesulphonate as the acidic catalyst, and at the reflux temperature, with azeotropic removal of water.

Alternatively, compounds of formula II wherein $R^3$ represents an alkyl group substituted by an alkoxy group can be prepared by the alkylation of corresponding compounds of formula II wherein one or both of the symbols $R^3$ represents an alkyl group substituted by a hydroxy group, the other symbols being as hereinbefore defined, by the application or adaptation of known methods, for example by reaction with sodium hydride followed by reaction with the appropriate alkyl halide.

Compounds of formula II wherein one or, more especially, both of the groups $R^3$ contain one or more moieties of the formula $-CH_2OH$, the other symbols being as hereinbefore defined, are preferably prepared by the reduction of corresponding compounds containing a group of the formula $-COOR^5$ (wherein $R^5$ represents an alkyl group of up to three carbon atoms, preferably ethyl or methyl) in place of the or each of the said moieties. The reduction may be carried out by the application or adaptation of known methods, for example by lithium aluminium hydride.

The compounds obtained by the abovementioned processes, including the intermediates, can be purified by the usual physical methods, in particular crystallization and chromatography, especially to resolve mixtures of enantiomers, for example using a chiral column.

According to a further feature of the present invention, compounds of general formula I are prepared by the interconversion of other compounds of general formula I. For example, compounds containing acyloxy groups can be prepared by the acylation of compounds containing hydroxy groups by the application or adaptation of known methods, for example by reaction with the appropriate acid anhydride, optionally in an inert solvent, e.g. dichloromethane, and optionally in the presence of a catalyst, such as 4-dimethylamino-pyridine.

According to a further feature of the invention, acid addition salts of compounds of formula I are prepared by reaction of the parent compounds of formula I with the appropriate acid, for example in an ethereal medium, e.g. tetrahydrofuran, diethyl ether or a mixture thereof.

As well as being useful in themselves as active compounds, acid addition salts of compounds of formula I are useful for the purposes of purification of the parent compounds of formula I, for example by exploitation of the solubility differences between the salts and the parent compounds, by techniques known to those skilled in art. The parent compounds of formula I can be regenerated from their acid addition salts by known methods, for example by treatment with an alkali, e.g. aqueous sodium bicarbonte solution or aqueous ammonia solution.

N-Benzylimidazoles of formula (III) may be prepared according to the method of H. J. M. Dou and J. Metzger, Bull. Soc. Chim. Fr., 1976. 1861.

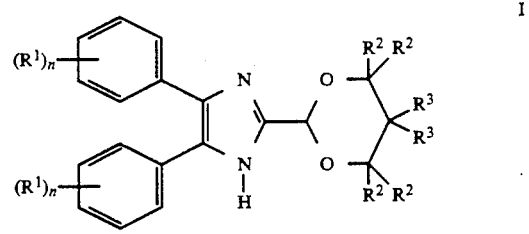

I

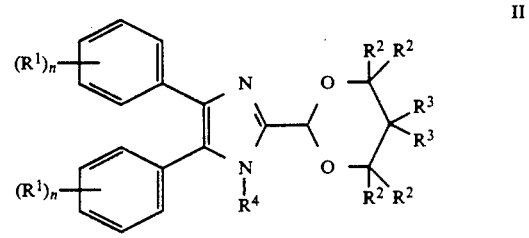

II

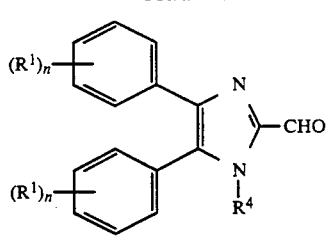

III

EXAMPLES

The following Examples illustrate the preparation of the compounds according to the invention and the Reference Examples illustrate the preparation of the intermediates.

In the nuclear magnetic resonance spectra (NMR) the chemical shifts are expressed in ppm relative to tetramethylsilane. Abbreviations have the following significances: s=singlet; d-doublet; t-triplet; q-quartet; m-multiplet; dd-doublet of doublets; dt-doublet of triplets. Infra-red spectra (IR) were obtained using the potassium bromide disc method.

EXAMPLE 1

Compound A

Liquid ammonia (100 ml) was condensed into a solution of 1-benzyl-2-(1,3-dioxan-2-yl)-4,5-dipehenylimidazole (5.5 g; prepared as described in Reference Example 2) in anhydrous tetrahydrofuran (100 ml). Small pieces of sodium were added portion wise to this mixture until TLC analysis (ethyl acetate) showed that reaction was complete.

The mixture was treated with solid ammonium chloride (5 g). After the ammonia had evaporated, the mixture was partitioned between saturated aqueous ammonium chloride solution (100 ml) and ethyl acetate (100 ml). The layers were separated and the organic layer was dried over magnesium sulphate and evaporated. Crystallization of the residue from a mixture of toluene and cyclohexane(1:1 v/v) gave 2-(1,3-dioxan-2-yl)-4,5-diphenylimidazole (3.0 g) in the form of cream-colored crystals, m.p. 203°–205° C. [Elemental analysis:-C,74.9; H,5.9;N,9.1%; calculated:-C,74.5;H,5.9;N,9.2%; NMR (CDCl$_3$):-1.44 and 2.06-2.36 (2H,2 m), 3.98 (2H,dt,J=14Hz and 3Hz), 4.23 (2H,dd,J=12Hz and 6Hz), 5.72 (1H,s), 7.30 & 7.50 (10H,m); IR (KBr):-696, 1109, 1360 and 3433 cm$^{-1}$].

EXAMPLE 2

Compound B

By proceeding in a manner similar to that described in Example 1, but replacing the 1-benzyl-2-(1,3-dioxan-2-yl)-4,5-diphenylimidazole by the appropriate quantity of 1-benzyl-2(5,5-dimethyl-1,3-dioxan-2-yl)-4,5-diphenylimidazole, prepared as described in Reference Example 2, there was prepared 2-(5,5-dimethyl-1,3-dioxan-2-yl)-4,5-diphenylimidazole, m.p. 166°–167° C. [Elemental analysis:- C,75.9;H,6.8;N,8.5%; calculated:-C,75.4;H,6.6;N,8.4%; NMR (CDCl$_3$):- 1.79 & 2.29 (6H,2s), 3.73 (4H,q,J=12Hz), 5.64 (1H,s), 7.2-7.6 (lOH,m); IR (KBr):-695, 764, 018, 1106, 1469, 2847 and 2952 cm$^{-1}$].

EXAMPLE 3

Compound C

By proceeding in a manner similar to that described in Example but replacing the 1-benzyl-2-(1,3-dioxan-2-yl)-4,5-diphenylimidazole by the appropriate quantity of (±)-cis/trans-1-benzyl-2-(4,6-dimethyl-1,3-dioxan-2-yl)-4,5-diphenylimidazole, prepared as described in Reference Example 2, there was prepared (±) -cis/trans-2-(4,6-dimethyl-1,3-dioxan-2-yl)-4,5-diphenylimidazole, m.p. 205°–206° C.

[Elemental analysis:- C,75.5;H,6.6;N,8.3%; calculated:-C,75.4;H,6.6;N,8.4%; NMR (CDCl$_3$);-1.32 and 1.35 (6H,2s), 1.25-2.10 (2H,m, 3.94-4.48 (2H,m), 5.78 an 6.18 (1H,2s), 7.20-7.60 (10H,m); IR (KBr):-697, 765, 1120, 1448, 2971 and 3499 cm$^{-1}$].

EXAMPLE 4

Compounds D, E, F. G, H, I, J, K, L, M, N, O, P and Q

Liquid ammonia (ca.400 ml) was condensed into a solution r-2-(1-benzyl-4,5-diphenylimidazol-2-yl)-c-5-hydroxymethyl-5-methyl-1,3-dioxane (4.9 g) in anhydrous tetrahydrofuran (50 ml). The mixture was carefully treated with small pieces of sodium until TLC analysis (ethyl acetate) showed that reaction was complete. The mixture was then treated with solid ammonium chloride (10 g). After the ammonia had evaporated, the mixture was treated with saturated aqueous ammonium chloride solution (100 ml); and the mixture was extracted with ethyl acetate (3×10ml). The combined extracts were washed with water (3×100 ml), dried over magnesium sulphate and evaporated. Crystallization of the residue from cyclohexane gave r-2-(4,5-diphenylimidazol-2-yl)-c-5-hydroxymethyl-5-methyl-1,3-dioxane (2.9 g) in the form of a colorless solid, m.p. 207°–209° C. [Elemental analysis:- C,71.5;H,6.4;N,7.8;H$_2$O,0.9%;  C$_{21}$H$_{22}$N$_2$O$_3$;0.2H$_2$O requires:-C,71.2;H,6.61;N,7.9;H$_2$O%; NMR (d$_6$-DMSO):-0.72 (3H,s), 3.60 (2H,d,J=12Hz), 3.73 (2H,d,J=6Hz), 3.97 (2H,d,J=12Hz), 4.21 (1H,t,J=6Hz), 5.57 (1H,s),7.2-7.5 (10H,m).

By proceeding in a similar manner, but replacing the r-2-(1-benzyl-4,5-diphenylimidazol-2-yl)-c-5-hydroxyethyl-5-methyl-1,3-dioxane by the appropriate quantities of the corresponding substituted 1-benzyl-2-(4,5-diphenylimidazol-2-yl)-1,3-dioxanes, there were prepared:

r-2-(4,5-diphenylimidazol-2-yl)-t-5-hydroxymethyl-5-methyl-1,3-dioxane, m.p. 208°–210° C.;
r-2-(4,5-diphenylimidazol-2-yl)-5-ethyl-c-5-hydroxymethyl-1,3-dioxane, m.p. 198°–200° C.;
r-2-(4,5-diphenylimidazol-2-yl)-t-5-methoxymethyl-5-methyl-1,3-dioxane, m.p. 190°–192° C.;
r-2-(4,5-diphenylimidazol-2-yl)-c-5-methoxymethyl-5-methyl-1,3-dioxane, m.p. 138°–140° C.;
r-2-(4,5-diphenylimidazol-2-yl)-5-ethyl-c-5-methoxymethyl-1,3-dioxane, m.p. 197°–199° C.;
cis-5-benzyl-2-(4,5-diphenylimidazol-2-yl)-1,3-dioxane, m.p. 209°–210° C.;
trans-5-benzyl-2-(4,5-diphenylimidazol-2-yl)-1,3-dioxane, m.p. 160°–161° C.;
2-(4,5-diphenylimidazol-2-yl)-1,3-dioxane-5-spirocyclohexane,m.p. 212°–214° C.;
2-(4,5-diphenylimidazol-2-yl)-1,3-dioxane-5-spirocyclohex-3'-ene, m.p. 221°–223° C.;

5,5-bis(ethoxymethyl)-2-(4,5-diphenylimidazol-2-yl)-1,3-dioxane, m.p. 128°-129° C.;

2-(4,5-diphenylimidazol-2-yl)-5,5-diethyl-1,3 dioxane, m.p. 210°-212° C.;

2-[4,5-bis(4-methoxyphenyl)imidazol-2-yl]-5,5-dimethyl-1,3-dioxane, m.p. 216°-218° C.; and 2-[4,5-bis(4-methylphenyl)imidazol-2-yl]-5,5-dimethyl-1,3-dioxane, m.p. 206°-209° C;

EXAMPLE 5

Hydrochlorides of Compounds D, B and E

A solution of r-2-(4,5-diphenylimidazol-2-yl)-c-5 hydroxymethyl-5-methyl-1,3-dioxane (1.7 g) in anhydrous tetrahydrofuran (30 ml) was treated slowly dropwise with saturated ethereal hydrogen chloride solution (60 ml). The resulting mixture was permitted to stand at room temperature for 20 minutes, and then the white precipitate was filtered off and washed with a small quantity of anhydrous diethyl ether, to give r-2-(4,5-diphenylimidazol-2-yl)-c-5-hydroxymethyl-5-methyl-1,3-dioxane hydrochloride (1.58 g), m.p. 275°-277° C. (with decomposition).

[Elemental analysis:- C.,62.7;H,5.9;N,7.1;Cl,12.8%$C_{21}H_{22}N_2O_3$HCl requires:-C,62.8;H,5.9;N,7.0;C12.4%;NMR (d6-DMSO):- 0.73 (3H,s), 3.66 (2H,S), 3.73 (2H,d,J=12Hz), 4.04 (2H,d,J=12Hz), 6.08 (1H,s), 7.44 (10H,s)].

By proceeding in a similar manner, but using 2-(5,5-dimethyl-1,3-dioxan-2-yl)-4,5-diphenylimidazole and r-2-(4,5-dipheylimidazol-2-yl)-t-5-hydroxymethyl-5-methyl-1,3-dioxane, respectively, there were prepared 2-(5,5-dimethyl-1,3-dioxan-2-yl)-4,5-diphenylimidazole hydrochloride, m.p. 225°-227° C, and r-2-(4,5-diphenylimidazol-2-yl)-t-5-hydroxymethyl-5-methyl-1,3-dioxane hydrochloride, m.p. 262°-264° C.

EXAMPLE 6

Compound R

A stirred solution of r-2-(4,5-diphenylimidazol-2-yl)-t-5-hydroxymethyl-5-methyl-1,3-dioxane (2.7 g) in dichloromethane at 0° C. was treated with acetic anhydride (5 ml) dropwise during a period of 15 minutes. The mixture was then treated with 4-dimethylaminopyridine (50 mg) and stirred at room temperature for one hour. It was then washed with water (3×100 ml), dried over magnesium sulphate, and concentrated to dryness. The result residue was recrystallized from ethyl acetate and washed with cyclohexane, to give t-5-acetoxymethyl-r-2-(4,5-diphenylimidazol-2-yl)-5-methyl-1,3-dioxane (2.4 g), in the form of a white solid, m.p.191°-193° C.

EXAMPLE 7

Compound S

By proceeding in a manner similar to that described hereinbefore in Example 4, but using 2-(1-benzyl-4,5-diphenylimidazol-2-yl)-5,5-bis(hydroxymethyl)-1,3-dioxane (prepared as described in Reference Example 6) as starting material, there was prepared 2-(4,5-diphenylimidazol-2-yl)-5,5-bis(hydroxymethyl)-1,3-dioxane, m.p. 228°-230° C.

REFERENCE EXAMPLE

A solution of 1-benzyl-4,5-diphenylimidazole (2.0 g) in anhydrous terrahydrofuran (25 ml) was flushed with argon and cooled in a bath of solid carbon dioxide and acetone (internal temperature below −70° C. Butyllithium (2.5M solution in hexane; 3.2 ml) was added dropwise over 5 minutes, maintaining the internal temperature at less than −60° C. The resulting black solution was stirred in the cooling bath for 10 minutes, then 1-formylmorpholine (1.5 g) was added dropwise during 1-2 minutes, again keeping the internal temperature at less than −60° C. The cooling bath was removed and the now almost colorless solution was allowed to warm to room temperature during a period of one hour. The solution was poured into hydrochloric acid (25 ml; 2M) and extracted with ethyl acetate (50 ml). the layers were separated and the ethyl acetate layer was washed with aqueous sodium bicarbonate solution (25 ml; 5% w/v), dried over magnesium sulphate and evaporated. Crystallization of the light yellow residue from acetone gave 1-benzyl-2-formyl-4,5-diphenylimidazole (1.0 g) in the form of off-white microcrystals, m.p. 146°-147° C.

REFERENCE EXAMPLE 2

A mixture of 1-benzyl-2-formyl-4,5-diphenylimidazole (6.8 g), propane-1,3-diol (7.6 g) and polymer-bound pyridinium 4-toluenesulphonate (1.0 g) in toluene (250 ml) was stirred at reflux under a Dean & Stark water trap for 8 hours. TLC analysis (using a 1:1 v/v mixture of ethyl acetate and hexane) showed about 20% unreacted aldehyde. A further quantity of polymer-bound pyridinium 4-toluenesulphonate (250 mg) and propane-1,3-diol (3.5 g) were added, and the mixture was heated at reflux for a further period of 6 hours. After cooling to room temperature the mixture was decanted from the catalyst and washed with water (3×100 ml). The organic solution was dried over magnesium sulphate and evaporated, to give 1-benzyl-2-(1,3-dioxan-2-yl)-4,5-diphenylimidazole (7.2 g), in the form of a pale pink solid.

By proceeding in a similar manner, but replacing the propane-1,3-diol by the appropriate quantities of 2,2-dimethylpropane-1,3-diol and (2-R,S, 4-R,S)-pentane-2,4-diol respectively, there were prepared 1-benzyl-2-(5,5-dimethyl-1,3-dioxan-2-yl)-4,5-diphenyl-imidazole and (±)-cis/trans-1-benzyl-2-(4,6-dimethyl-1,3-dioxan-2-yl)-4,5-diphenylimidazole.

REFERENCE EXAMPLE 3

A mixture of 1-benzyl-2-formyl-4,5-diphenylimidazole (13.5 g), 1,1,1-trishydroxymethylethane (24 g) and pyridinium 4-toluenesulphonate (1.0 g) in toluene (400 ml) was stirred at reflux under a Dean & Stark water trap for 7 hours. After cooling to room temperature the mixture was washed with water (3×200 ml), and the organic layer was dried over magnesium sulphate and evaporated, to give a pale yellow residue (14 g) which was subjected to flash chromatography on silica gel, eluting with a mixture of ethyl acetate and cyclohexane (1:1 v/v) to give, in order of elution: recovered 1-benzyl-2-formyl-4,5-diphenylimidazole (1.2 g); r-[1-benzyl-2-(4,5-diphenylimidazol-2-yl)]-c-5-hydroxymethyl-5-methyl-1,3-dioxane (5.8 g); and r-[1-benzyl]-2-(4,5-diphenylimidazol-2-yl)]-t-5-hydroxymethyl-5-methyl-1,3-dioxane (4.0 g).

REFERENCE EXAMPLE 4

A solution of2-(1-benzyl-4,5-diphenylimidazol-2-yl)-c-5-hydroxymethyl-5-methyl-1,3-dioxane (5.0 g) in anhydrous dimethylformamide (40 ml) was cooled to 5° C. and treated with sodium hydride (0.65 g of an 80% dispersion in oil). The mixture was stirred at room temperature for 1 hour, and then it was treated with methyl iodide (1.7 ml). The mixture was stirred at room temperature for a further 2 hours, and then it was partitioned between ethyl acetate (50 ml) and water (50 ml). The layers were separated and the aqueous layer was extracted with ethyl acetate (50 ml). The combined organic phases were dried over magnesium sulphate and evaporated to dryness. Crystallization of the residue from cyclohexane 9ave 2-(1-benzyl-4,5-diphenyl-midazol-2-yl)-c-5-methoxymethyl-5-methyl-1,3-dioxane (2.4 g), m.p. 138°–140° C.

REFERENCE EXAMPLE 5

By proceeding in a manner similar to that described hereinbefore in Reference Example 2, but replacing the propane-1,3-diol used as a starting material by the appropriate quantity of diethyl bis(hydroxymethyl)malonate, there was prepared 2-(1-benzyl-4,5-diphenylimidazol-2-yl)-5,5-diethoxy-1,3-dioxane.

REFERENCE EXAMPLE 6

A stirred solution of 2-(1-benzyl-4,5-diphenyl-imidazol-2-yl)-5,5-diethoxy-1,3-dioxane(6.0 g) in dry tetrahydrofuran (200 ml) under nitrogen was treated with a solution of lithium aluminium hydride in tetrahydrofuran (15.7 ml; 1.0M) dropwise, during 20 minutes, and keeping the temperature below 35° C. The mixture wa stirred at room temperature for 2 hours, and then it was treated with aqueous sodium hydroxide solution (8 ml; 3% w/v) filtered and evaporated. The resulting residue was recrystallized from ethyl acetate, to give 2-(1-benzyl-4,5-diphenylimidazol-2-yl)-5,5-bis(hydroxymethyl)-1,3-dioxane (3.45 g) in the form of a colorless Crystalline solid, m.p. 186°–188° C.

The present invention also includes within its scope pharmaceutical formulations which comprise at least one of the compounds of formula I or a pharmaceutically acceptable salt thereof in association with a pharmaceutically acceptable carrier or coating. In clinical practice, the compounds of the present invention may be administered parenterally, rectally or orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavoring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilizing, preserving, wetting, emulsifying and dispersing agents. They may be sterilized, for example, by filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing at least one compound of formula (I).

The percentage of active ingredient in the compositions of the invention may be varied, it being necessary that it should constitute a proportion such that a suitable dosage shall be obtained. Obviously, several unit dosage forms may be administered at about the same time. The dose used will be determined by the physician; and depends upon the desired therapeutic effect, the route of administration and the duration of the treatment, and the condition of the patient. In the adult, the doses are generally from 0.5 to 70, preferably 1 to 10, mg/kg body weight per day by oral administration.

The following Composition Example illustrates pharmaceutical compositions according to the present invention.

COMPOSITION EXAMPLE

| No. 2 size gelatin capsules each containing: | |
| --- | --- |
| -2-(5,5-dimethyl-1,3-dioxan-2-yl)-4,5-diphenyl-imidazole | 20 mg |
| lactose | 100 mg |
| starch | 60 mg |
| dextrin | 40 mg |
| magnesium stearate | 1 mg | were prepared in accordance with the known procedure.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the intended spirit and scope of the appended claims. The above references are hereby incorporated by reference.

We claim:

1. An imidazole derivative of formula:

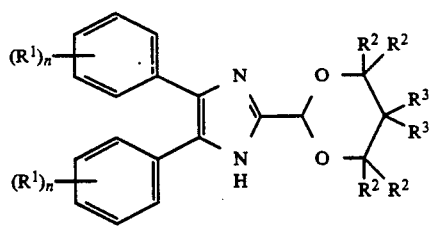

wherein the symbols $R^1$ are the same or different and each represents a halogen atom or an alkyl or alkoxy group containing from 1 to 3 carbon atoms, the symbols n are the same or different and each represents 0 or an integer from 1 to 5, the symbols $R^3$ are the same or different and each represents a hydrogen atom or an alkyl group containing from 1 to 3 carbon atoms, and the symbols $R^2$ are the same or different and each represents a hydrogen atom or an alkyl group containing from 1 to 3 carbon atoms optionally substituted by at least one halogen atom, by a hydroxy or acyloxy group, by an alkoxy group containing from 1 to 3 carbon atoms which itself is optionally substituted by a hydroxy or acyloxy group, or by a phenyl group which itself is optionally substituted by at least one substituent selected from halogen atoms and alkyl and alkoxy groups each containing up to 3 carbon atoms, or together the symbols $R^3$ and the carbon atom to which they are both attached form a cycloalkane or cycloalkene group containing from 5 to 7 carbon atoms, and pharmaceutically acceptable acid addition salts thereof.

2. A derivative according to claim 1, wherein $R^1$ is halogen or alkyl, n is 0 or 1 and $R^2$ and $R^3$ each represent hydrogen or alkyl.

3. A derivative according to claim 1, wherein the groups $R^1$ are identical and the symbols n are identical.

4. A derivative according to claim 1, wherein n is 0 or 1 and, when n is 1, the group $R^1$ is in the para-position of the phenyl group to which it is attached.

5. A derivative according to claim 1, wherein at least one of each geminal pair of symbols $R^2$ represents a hydrogen atom and symbols $R^2$ which do not represent hydrogen atoms are identical.

6. A derivative according to claim 1, wherein at least one of the symbols has a value selected from the following:
   (i) n represents 0 or 1;
   (ii) $R^1$ represents a methyl or methoxy group;
   (iii) $R^2$ represents a hydrogen atom or a methyl group; and
   (iv) $R^3$ represents a hydrogen atom or an alkyl group containing 1 or 2 carbon atoms optionally substituted by a hydroxy, acyloxy, methoxy or phenyl group, or together the symbols $R^3$ and the carbon atom to which they are both attached form a cyclohexane or cyclohexane group.

7. A derivative according to claim 1, selected from:
A: 2-(1,3-dioxan-2-yl)-4,5-diphenylimidazole;
B: 2-(5,5-dimethyl-1,3-dioxan-2-yl)-4,5-diphenylimidazole;
C: (±)-cis/trans-2-(4,6-dimethyl-1,3-dioxan-2-yl)-4,5-diphenylimidazole;
D: r-2-(4,5-diphenylimidazol-2-yl)-c-5-hydroxymethyl-5-methyl-1,3-dioxane;
E: r-2-(4,5-diphenylimidazol-2-yl)-t-5-hydroxymethyl-5-methyl-1,3-dioxane;
F: r-2-(4,5-diphenylimidazol-2-yl)-5-ethyl-c-5-hydroxymethyl-1,3-dioxane;
G: r-2-(4,5-d iphenylimidazol-2-yl)-t-5-methoxymethyl-5-methyl-1,3-dioxane;
H: r-2-(4,5-diphenylimidazol-2 -yl)-c-5-methoxymethyl-5-methyl-1,3-dioxane;
I: r-2-(4,5-diphenylimidazol-2-yl)-5-ethyl-c-5-methoxymethyl-1,3-dioxane;
J: cis-5-benzyl-2-(4,5-diphenylimidazol-2-yl)-1,3-dioxane;
K: trans-5-benzyl-2-(4,5-diphenylimidazol-2-yl)-1,3-dioxane;
L: 2-(4,5-diphenylimidazol-2-yl)-1,3-dioxane-5-spiro-cyclohexane;
M: 2-(4,5-diphenylimidazol-2-yl)-1,3-dioxane-5-spiro-cyclohex-3'-ene;
N: 5,5-bis(ethoxymethyl)-2-(4,5-diphenylimidazol-2yl)-1,3-dioxane;
O: 2-(4,5-diphenylimidazol-2-yl)-5,5-diethyl-1,3-dioxane;
P: 2-[4,5-bis(4-methoxyphenyl)imidazol-2-yl]-5,5-1-1,3-dioxane;
Q: 2-[4,5-bis(4-methylphenyl)imidazol-2-yl]-5,5-dimethyl-1,3-dioxane;
R: t-5-acetoxymethyl-r-2-(4,5-diphenylimidazol-2-yl)-5-methyl-1,3-dioxane; or
S: 2-(4,5-diphenylimidazol-2-yl)-5,5-bis(hydroxymethyl)-1,3-dioxane or a pharmaceutically acceptable acid addition salt thereof.

8. A pharmaceutical composition comprising an imidazole derivative of formula (I) as defined in claim 1 or a pharmaceutically acceptable acid addition salt thereof in association with a pharmaceutically acceptable carrier or coating.

9. A method for the treatment of atherosclerosis. hyperlipidemia, cholesterol ester storage disease or atheroma in vein grafts comprising administering an effective amount of an imidazole derivative of formula (I) as defined in claim 1 or a pharmaceutically acceptable acid addition salt thereof.

* * * * *